United States Patent
Nuopponen et al.

(10) Patent No.: US 10,307,722 B2
(45) Date of Patent: Jun. 4, 2019

(54) METHOD FOR REDUCING THE VISCOSITY OF A NANOFIBRILLAR CELLULOSE HYDROGEL

(71) Applicant: UPM-Kymmene Corporation, Helsinki (FI)

(72) Inventors: Markus Nuopponen, Helsinki (FI); Isko Kajanto, Espoo (FI); Anne Meriluoto, Helsinki (FI); Kari Luukko, Espoo (FI); Lauri Paasonen, Järvenpää (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 0 days.

(21) Appl. No.: 15/538,515

(22) PCT Filed: Dec. 21, 2015

(86) PCT No.: PCT/FI2015/050921
§ 371 (c)(1),
(2) Date: Jun. 21, 2017

(87) PCT Pub. No.: WO2016/102769
PCT Pub. Date: Jun. 30, 2016

(65) Prior Publication Data
US 2017/0354944 A1    Dec. 14, 2017

(30) Foreign Application Priority Data
Dec. 22, 2014 (FI) .................................. 20146136

(51) Int. Cl.
*C12N 1/22* (2006.01)
*D21H 11/18* (2006.01)
(Continued)

(52) U.S. Cl.
CPC ....... *B01J 13/0069* (2013.01); *B01J 13/0056* (2013.01); *C12N 1/22* (2013.01);
(Continued)

(58) Field of Classification Search
CPC ... B01J 13/0069; B01J 13/0056; D21H 11/18; D21H 11/20; C12N 5/0018; C12N 1/221;
(Continued)

(56) References Cited

FOREIGN PATENT DOCUMENTS

WO    2012056109 A2    5/2012
WO    2012107648 A1    8/2012
(Continued)

OTHER PUBLICATIONS

Lou, Y. et al., "The use of nanofibrillar cellulose hydrogel as a flexible three-dimensional model to culture human pluripotent stem cells", Stems Cells and Development, Feb. 2014, vol. 23, No. 4, pp. 380-392.
(Continued)

*Primary Examiner* — William K Cheung
(74) *Attorney, Agent, or Firm* — Nixon Peabody LLP

(57) ABSTRACT

The invention relates to a method for reducing the viscosity of a nanofibrillar cellulose hydrogel, wherein the method comprises mixing a nanofibrillar cellulose hydrogel with an aqueous growth medium for cell culture, wherein the aqueous growth medium contains one or more salts and optionally one or more sugars, using shearing forces so that a homogeneous dispersion is formed. The invention further relates to a dispersion comprising a nanofibrillar cellulose hydrogel and an aqueous growth medium for cell culture and to a use of an aqueous growth medium.

20 Claims, 1 Drawing Sheet

(51) Int. Cl.
  *D21H 11/20* (2006.01)
  *B01J 13/00* (2006.01)
  *C12N 5/00* (2006.01)

(52) U.S. Cl.
  CPC ............ *C12N 5/0018* (2013.01); *D21H 11/18* (2013.01); *D21H 11/20* (2013.01); *C12N 2500/05* (2013.01); *C12N 2500/34* (2013.01); *C12N 2521/00* (2013.01); *C12N 2533/78* (2013.01)

(58) Field of Classification Search
  CPC ............ C12N 2533/78; C12N 2521/00; C12N 2500/05; C12N 2500/34
  USPC .......................................................... 516/106
  See application file for complete search history.

(56) References Cited

FOREIGN PATENT DOCUMENTS

| | | |
|---|---|---|
| WO | 2013093197 A1 | 6/2013 |
| WO | 2013093198 A1 | 6/2013 |
| WO | 2013093199 A1 | 6/2013 |
| WO | 2014049204 A1 | 4/2014 |
| WO | WO 2014/049204 A1 * | 4/2014 |

OTHER PUBLICATIONS

Ono, H. et al., 1H Spin-spin relaxation time of water and rheological properties of cellulose nanofiber dispersion, transparent cellulose hydrogel (TCG), Polymer Journal, 2004, vol. 36, No. 9, pp. 684-694.

Madhushree Bhattacharya et al., "Nanofibrillar cellulose hydrogel promotes three-dimensional liver cell culture", Journal of Controlled Release, vol. 164, No. 3, Dec. 1, 2012.

Malinen Melina M. Et. al., "Differentiation of liver progenitor cell line to functional organotypic cultures in 3D nanofibrillar cellulose and hyaluronan-gelatin hydrogels", Biomaterials, vol. 35, No. 19, Apr. 1, 2014.

Syverud Kristin et al., "Controlling the elastic modulus of cellulose nanofibril hydrogels-scaffolds with potential in tissue enginee", Cellulose, Springer, Netherlands, vol. 22, No. 1, Oct. 17, 2014, pp. 473-481.

International Search Report from International Application No. PCT/FI2015/050921 dated Apr. 4, 2016.

International Preliminary Report on Patentability from International Application No. PCT/FI2015/050921 dated Dec. 9, 2016.

Search Report from Patent Application No. 20146136 dated Apr. 15, 2015.

Fukuzumi, et al., "Dispersion stability and aggregation behavior of TEMPO-oxidized cellulose nanofibrils in water as a function of salt addition", Cellulose, 2014, 21: 1553-1559.

* cited by examiner

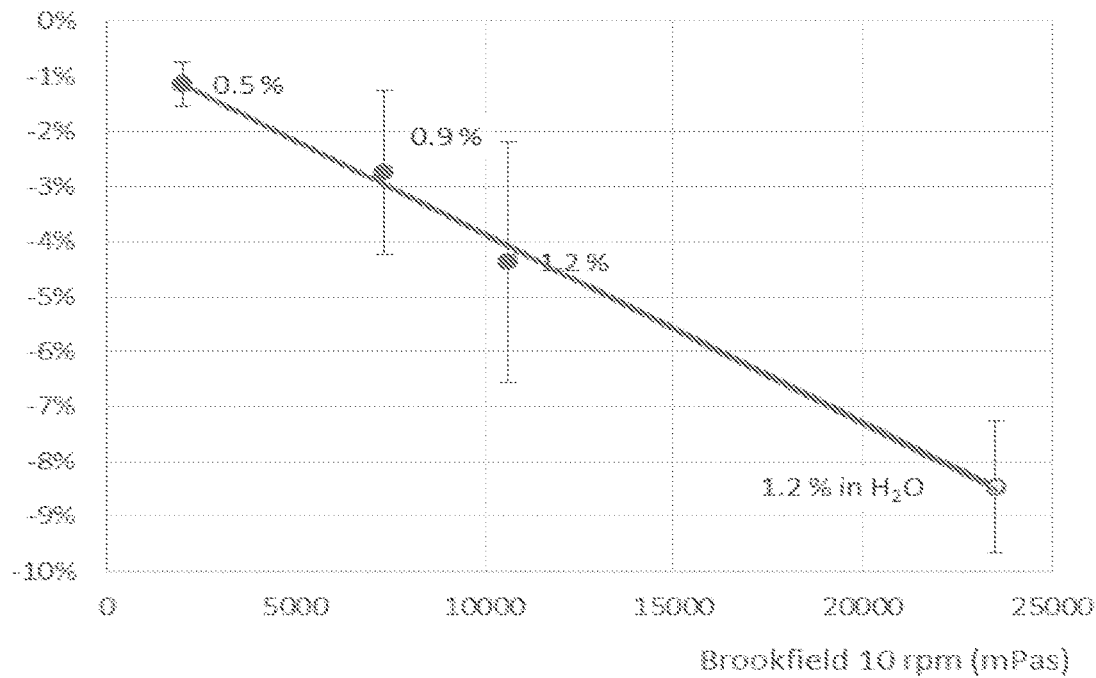

METHOD FOR REDUCING THE VISCOSITY OF A NANOFIBRILLAR CELLULOSE HYDROGEL

CROSS-REFERENCE TO RELATED APPLICATIONS

This application is a U.S. National Stage of International Application No. PCT/FI2015/050921, filed on Dec. 21, 2015, which claims priority to Finnish Patent No. 20146136, filed Dec. 22, 2014, the contents of each of which are incorporated herein by reference in their entireties.

FIELD OF THE INVENTION

The invention relates to a method for reducing the viscosity of a nanofibrillar cellulose hydrogel, to a nanofibrillar cellulose hydrogel and to the use of an aqueous growth medium for cell culture.

BACKGROUND

Nanofibrillar cellulose hydrogel is used in 3D cell culture. Typically the nanofibrillar cellulose is delivered as a stiff hydrogel dispersion. The stiff hydrogel may be difficult to handle and to dilute, especially by pipetting. Often users of the hydrogel try to dilute it for cell culturing. There is, in many cases, a need to adjust the viscosity of the nanofibrillar cellulose hydrogel during the production to facilitate handling. At the same time, however, gel strength has to be high enough for cell culturing applications.

There is therefore a need to provide a method for reducing the viscosity of nanofibrillar cellulose hydrogel and for a nanofibrillar cellulose hydrogel that is easier to handle.

PURPOSE

The purpose is to provide a new type of method for reducing the viscosity of nanofibrillar cellulose hydrogel. Further, the purpose of the invention is to provide a new type of a dispersion comprising a nanofibrillar cellulose hydrogel and an aqueous growth medium and a new use of an aqueous growth medium for reducing the viscosity of a nanofibrillar cellulose hydrogel.

SUMMARY

The method is characterized by what is presented in claim 1.

The dispersion is characterized by what is presented in claim 12.

The multiwell plate or kit is characterized by what is presented in claim 22.

The use of an aqueous growth medium for reducing the viscosity of a nanofibrillar cellulose hydrogel is characterized by what is presented in claim 23.

The use of the dispersion is characterized by what is presented in claims 27 and 28.

The dispersion for use in therapy is characterized by what is presented in claim 29.

BRIEF DESCRIPTION OF THE DRAWINGS

The accompanying drawings, which are included to provide a further understanding of the invention and constitute a part of this specification, illustrate embodiments of the invention and together with the description help to explain the principles of the invention. In the drawings:

The figure is a graph illustrating pipetting errors and viscosities measured from different concentrations of nanofibrillar cellulose hydrogel diluted with an aqueous growth medium.

DETAILED DESCRIPTION

A method for reducing the viscosity of a nanofibrillar cellulose hydrogel comprises mixing a nanofibrillar cellulose hydrogel with an aqueous growth medium for cell culture, wherein the aqueous growth medium contains one or more salts and optionally one or more sugars, using shearing forces so that a homogeneous dispersion is formed.

The expression "nanofibrillar cellulose" of "NFC" should be understood in this specification, unless otherwise stated, as referring to a collection of isolated cellulose nanofibrils (CNF) and/or nanofibril bundles derived from a cellulose-based fiber material.

Nanofibrils typically have a high aspect ratio. The length might exceed one micrometer, while the diameter is typically below 200 nm. The smallest nanofibrils are similar to so-called elementary fibrils, which are typically approx. 2-12 nm in diameter. The dimensions and size distribution of the fibrils or fibril bundles are dependent on the raw material, pretreatment and the disintegration method and efficiency. Typically the median length of fibrils or fibril bundles in NFC is not greater than 100 μm, for example in the range of 1-50 μm, and the number average diameter of the fibrils or fibril bundles is smaller than 200 nm, suitably in the range of 2-100 nm. Depending on the raw material source, e.g. hardwood (HW) vs. softwood (SW) pulp, different polysaccharide compositions may exist in the final NFC product. The nanofibrillar celluloses may contain hemicelluloses and lignin in varying amounts, depending on plant source and pulping conditions. For example, bleached birch pulp has a high xylose content (25% by weight) and a negligible lignin content. Nanofibrillar celluloses are complex mixtures of different polysaccharide structures.

Cellulose pulp fibers may be obtained from a cellulose-based fibre material. The expression "cellulose-based fibre material" should be understood in this specification, unless otherwise stated, as referring to any raw material source that contains cellulose and from which cellulose pulp fibers, and subsequently nanofibrillar cellulose, can be produced.

The cellulose-based fibre material may, in principle, be based on any plant material that contains cellulose. The plant material may be wood. The wood can be from a softwood tree such as spruce, pine, fir, larch, douglas-fir or hemlock, or from a hardwood tree such as birch, aspen, poplar, alder, *eucalyptus* or acacia, or from a mixture of softwoods and hardwoods. Non-wood material may be derived from agricultural residues, grasses or other plant substances such as straw, leaves, bark, seeds, hulls, flowers, vegetables or fruits from cotton, corn, wheat, oat, rye, barley, rice, flax, hemp, manila hemp, sisal hemp, jute, ramie, kenaf, bagasse, bamboo or reed. Nanofibrillar cellulose may also contain hemicelluloses; the amount is dependent on the plant source.

The cellulose-based fiber material can be formed by isolating cellulose fibers from raw material that contains cellulose by chemical, mechanical, thermo-mechanical, or chemi-thermo-mechanical pulping processes, and by conventional bleaching processes. The cellulose-based fiber material may not contain substantial amounts of lignin, or it may contain only traces of lignin or non-detectable amounts of lignin. Thus also the NFC may be essentially lignin-free.

The cellulose-based fiber material may be pretreated to make the material more susceptible to the disintegration into nanofibrils. Such pretreatment may be ion-exchange of carboxyl groups with $Na^+$, or enzymatic or chemical modification, such as a chemical modification increasing the electric charge of the cellulose-based fiber material. The chemical modification increasing the electric charge may be an anionic modification such as carboxymethylation or oxidization, such as n-oxyl mediated catalytic oxidation, such as TEMPO-mediated oxidation, or a cationic modification. The term native cellulose refers here to any cellulose-based fiber material, which has not been chemically modified after the pulping process and the optional bleaching process; both ion-exchanged and enzymatically pretreated celluloses are regarded as native celluloses. NFC liberated from anionically modified, cationically modified or native cellulose-based fiber material is referred to as anionic, cationic or native NFC, respectively. Different types of cellulose-based fiber material may also be combined before fibrillation to obtain mixed NFC grades.

The cellulose-based fibre material may, in the context of this specification, also include cellulose-based raw material that comprises ribbon-like microfibrils derived from a bacterial fermentation processes. The cellulose based raw material may also be derived from a cellulose-producing micro-organism. The micro-organism may be of the genus *Acetobacter, Agrobacterium, Rhizobium, Pseudomonas* or *Alcaligenes*, preferably of the genus *Acetobacter*, and more preferably of the species *Acetobacter xylinum* or *Acetobacter pasteurianus*.

Cellulose consists, in the context of this specification, essentially of type I cellulose.

The cellulose-based fiber material comprises crystalline and amorphous regions. Cellulose crystallinity refers to the percentage of all the cellulose occupied in the crystalline region. The crystallinity of the cellulose-based fiber material used as starting material may be at least 50%. Suitably the crystallinity of the cellulose pulp is at least 55%.

Nanofibrillar cellulose is characterized by very high water retention values, a high degree of chemical accessibility and the ability to form stable gels, hydrogels, in water or other polar solvents. A nanofibrillar cellulose product is typically a dense network of highly fibrillated cellulose.

The fiber material suspension that is subjected to fibrillation is an aqueous mixture of fiber material, also herein called as pulp. The fiber material may contain whole fibers, parts (fragments) separated from them, fibril bundles, or fibrils. Typically the fiber material suspension is a mixture of such elements, in which the ratios between the components are dependent on the degree of processing or on the treatment stage, for example the number of runs or "passes" through the treatment of the same batch of fiber material.

The dimensions of the fibrils or fibril bundles of the NFC are dependent on the raw material and the fibrillation method. The term fibrillation may be used interchangeably with expression disintegration, and generally refers to disintegrating cellulose-based fiber material mechanically by work applied to the fibers, where cellulose fibrils are liberated from the fibers or fiber fragments. The work may be based on various effects, like grinding, crushing or shearing, or a combination of these, or another corresponding action that delaminates the cell walls of the fibers and liberates fibrils. The energy taken by the refining work is normally expressed in terms of energy per processed raw material quantity, in units of e.g. kWh/kg, MWh/ton, or units proportional to these. Mechanical disintegration of the cellulose raw material may be carried out with any suitable equipment such as a refiner, grinder, disperser, homogenizer, colloider, friction grinder, pin mill, rotor-rotor dispergator, ultrasound sonicator, fluidizer such as microfluidizer, macrofluidizer or fluidizer-type homogenizer. The disintegration is performed at conditions wherein water is sufficiently present to prevent the formation of bonds between the fibers. Typically the NFC hydrogel is manufactured in a consistency of from 0.05 to 10% w/w, such as from 0.1 to 4% w/w, such as from 0.12 to 1.2% w/w, said consistencies being convenient for the fibrillation and the handling of the NFC hydrogel.

Different grades of NFC may be categorized based on three main properties: (i) size distribution, length and diameter (ii) chemical composition, and (iii) rheological properties. To fully describe a grade the properties may be used in parallel. Examples of different grades include native NFC, oxidized NFC (high viscosity), carboxymethylated NFC, sulphonated NFC, and cationized NFC. Within these main grades, also sub-grades exist, for example: extremely well fibrillated vs. moderately fibrillated, high degree of substitution vs. low, low viscosity vs. high viscosity etc.

The fibrillation technique and the pretreatment may have an influence on the fibril size distribution. Typically, native grades have a wider fibril diameter (for example a number average diameter in the range of 2-100 nm, or 7-50 nm) while chemically modified grades are thinner (for example a number average diameter in the range of 2-20 nm). Size distribution may also be narrower for the chemically modified grades. Certain modifications, especially TEMPO-oxidation, yield shorter fibrils. The diameter of a fibril may be determined with several techniques, such as by using a microscope. Fibril thickness and width distribution may be measured by image analysis of images from a field emission scanning electron microscope (FE-SEM), a transmission electron microscope (TEM), such as a cryogenic transmission electron microscope (cryo-TEM), or an atomic force microscope (AFM). In general AFM and TEM suit best for NFC grades with narrow fibril diameter distribution.

Nanofibrillar cellulose is characterized by a large specific surface area and a strong ability to form hydrogen bonds. Hydrophilicity of nanofibrillar cellulose is due to the presence of hydroxyl groups in the glucoside rings and partially charged hemicellulose moieties. In an aqueous environment, a dispersion of cellulose nanofibers forms a viscoelastic hydrogel network. The hydrogel is formed at relatively low concentrations of for example 0.05-0.2% w/w by dispersed and hydrated entangled fibrils. The efficacy of the mixing may influence to fine structure of the gel, i.e. more homogeneous gels are obtained with more efficient mixing apparatus. Since the gel structure is highly dependent on shear history of the sample, either continuous or discontinuous structures of gel clumps can be achieved depending on the mixing method after dilution. Typical for homogeneous and continuous gel structures is high yield stress even at low concentrations. Respectively, discontinuous gel structures have typically a lower yield stress value when compared to well dispersed, homogeneous gels even at the same concentration.

As regards rheology, the NFC hydrogels are shear-thinning materials, which means that their viscosity depends on the speed (or force) by which the material is deformed. When measuring the viscosity in a rotational rheometer, the shear-thinning behavior is seen as a decrease in viscosity with increasing shear rate. The hydrogels show plastic behavior, which means that a certain shear stress (force) is required before the material starts to flow readily. This critical shear stress is often called the yield stress. The yield stress can be determined from a steady state flow curve measured with a stress controlled rheometer. When the viscosity is plotted as function of applied shear stress, a dramatic decrease in viscosity is seen after exceeding the critical shear stress. The zero shear viscosity and the yield stress are the most important rheological parameters for verifying the success of fibrillation and for describing the suspending power of the materials. These two parameters separate different grades quite clearly and thus enable classification of the grades. The zero-shear viscosity of nanofibrillar celluloses may vary from 100 to 100 000 Pa·s, typically the zero-shear viscosity varies from 1000 to 50 000 Pa·s, in water at 0.5 wt % concentration. The yield stress of the nanofibrillar celluloses may vary from 0.5 to 50 Pa, typically 1 to 20 Pa, in water at 0.5 wt % concentration.

Rheological measurements of the samples in the form of NFC hydrogels may be carried out with a stress controlled rotational rheometer (ARG2, TA instruments, UK) equipped with four-bladed vane geometry. Samples are diluted with deionized water (200 g) to a concentration of 0.5 wt % and mixed. Rheometer measurement is carried out for the sample. The diameters of the cylindrical sample cup and the vane are 30 mm and 28 mm, respectively, and the length was 42 mm. The steady state viscosity of the hydrogels is measured using a gradually increasing shear stress of 0.001-1000 Pa. After loading the samples to the rheometer they are allowed to rest for 5 min before the measurement is started, room temperature. The steady state viscosity is measured with a gradually increasing shear stress (proportional to applied torque) and the shear rate (proportional to angular velocity) is measured. The reported viscosity (=shear stress/shear rate) at a certain shear stress is recorded after reaching a constant shear rate or after a maximum time of 2 min. The measurement is stopped when a shear rate of 1000 s−1 is exceeded. The method is used for determining zero-shear viscosity and yield stress.

Nanofibrillar cellulose may also be characterized by Brookfield viscosity. The apparent viscosity of the NFC is measured with a Brookfield viscometer (Brookfield viscosity) or another corresponding apparatus. Suitably a vane spindle (number 73) is used. There are several commercial Brookfield viscometers available for measuring apparent viscosity, which all are based on the same principle. Suitably a RVDV spring (Brookfield RVDV-III) is used in the apparatus. A sample of the nanofibrillar cellulose is diluted to a concentration of 0.8 wt % in water and mixed for 10 min using a propel mixer 700-800 rpm. No ultrasound mixing is used for modified grades. The diluted sample mass is added to a 250 ml beaker and the temperature is adjusted to 20° C.±1° C., heated if necessary and mixed. The spindle is inserted in the beaker and measuring started. In this specification, all Brookfield viscosity values are given at low rotational speed 10 rpm. Brookfield viscosity of the nanofibrillar celluloses may vary from 2000 to 60 000 mPa·s, and typically the Brookfield viscosity varies from 5000 to 40 000 mPa·s, in water at concentration of 0.8 wt %.

Nanofibrillar cellulose may also be characterized by turbidity, which correlates with the fineness of the fibrils, as thinner fibrils scatter light poorly. For example, NFC having a number average diameter of 1-40 nm provides transparency to the hydrogel. The term "turbidity" should be understood as referring to the cloudiness of a fluid caused by individual particles (total suspended or dissolved solids). Turbidity may be measured quantitatively using optical turbidity measuring instruments. There are several commercial turbidometers available for measuring quantitatively turbidity. In the context of this specification, a method based on nephelometry is used. The units of turbidity from a calibrated nephelometer are called Nephelometric Turbidity Units (NTU). The measuring apparatus (turbidometer) is calibrated and controlled with standard calibration samples, followed by measuring of the turbidity of the diluted NFC sample. In one turbidity measurement method, a NFC sample is diluted in water, to a concentration below the gel point of said NFC, and the turbidity of the diluted sample is measured. Said concentration where the turbidity of the NFC samples is measured is 0.1 wt %. HACH P2100 Turbidometer with a 50 ml measuring vessel is used. The dry matter of the NFC sample is determined (e.g. according ISO 4119/1995 with the exception that t=16 h) and 0.5 g of the sample, calculated as dry matter, is loaded in the measuring vessel, which is filled with tap water to 500 g and vigorously mixed by shaking for about 30 s. Without delay the aqueous mixture is divided into 5 measuring vessels, which are inserted in the turbidometer. Three measurements on each vessel are carried out. The mean value and standard deviation are calculated from the obtained results, and the final result is given as NTU units. Turbidity of the nanofibrillar celluloses may vary from 1 to 200 NTU, and typically the turbidity varies from 3 to 150 NTU, in water at concentration of 0.1 wt %. Typically, anionic NFC hydrogels are more transparent when compared to native grades due to smaller fibril diameters.

One way to characterize NFC is to define both the viscosity and the turbidity. In general, as the fibrillation degree increases, the viscosity increases and at the same time the turbidity decreases.

In one example, the turbidity of anionic NFC is at most 90 NTU, for example from 3 to 60 NTU, measured at a consistency of 0.1 wt % in water. In one example, the turbidity of native NFC may be at most 200 NTU, for example from 80 to 150 NTU, measured at a consistency of 0.1 wt % in water. To characterize the NFC grade these ranges may be combined with the viscosity ranges of the NFC grade. In one example, the zero-shear viscosity of anionic NFC is at least 1000 Pa·s, for example from 5000 to 30 000 Pa·s, in water at 0.5 wt % concentration. In one example, the zero-shear viscosity of native NFC is at least 100 Pa·s, for example from 300 to 8 000 Pa·s, in water at 0.5 wt % concentration.

The cellulose may be oxidized. In the oxidation of cellulose, the primary hydroxyl groups of cellulose may be oxidized catalytically by a n-oxyl or heterocyclic nitroxyl compound, for example 2,2,6,6-tetramethylpiperidinyl-1-oxy free radical, commonly called "TEMPO". The primary hydroxyl groups (C6-hydroxyl groups) of the cellulosic β-D-glucopyranose units are selectively oxidized to carboxylic groups. Some aldehyde groups may also be formed from the primary hydroxyl groups. When the fibers of oxidized cellulose thus obtained are disintegrated in water, they may give a stable transparent dispersion containing essentially only individualized cellulose fibrils. With oxidized pulp as the starting medium, it is possible to obtain NFC whose Brookfield viscosity measured at a consistency of 0.8% is at least 10 000 mPa·s, for example in the range of 10 000-40000 mPa·s. The expression "hydrogel" or "nanofibrillar cellulose hydrogel" should be understood in this specification, unless otherwise stated, as referring to an aqueous dispersion of nanofibrillar cellulose having a continuous gel structure, or a structure of discontinuous hydrogel clumps. The storage modulus (G') value of the nanofibrillar cellulose hydrogel is greater than its loss modulus (G") value, i.e. the loss tangent is <1. The loss tangent may be <1 at least up to strain value 10%.

The viscoelastic properties storage modulus G', loss modulus G" and loss tangent (G"/G') of the NFC hydrogels may be determined with the frequency sweep in dynamic oscillation mode of the rheometer (strain 1% and 10%, frequency 0.1-100, temperature 25° C.). The stress sweep is measured in a shear stress range of 0.001-100 Pa at the frequency 0.1 Hz, at 25° C. and at a neutral pH. For determining whether a certain material is a gel, i.e. whether its loss tangent is <1 (Frequency sweep, 1 rad/s, 1% strain), the measurement is performed in the same way except in the consistency of the material (i.e. the material is not diluted prior to measurement). The storage modulus of nanofibrillar celluloses may vary from 0.1 to 100 Pa, typically the storage modulus varies from 1 to 50 Pa, in water at 0.5 wt % concentration.

An "aqueous growth medium" should, in the context of this specification, be understood as referring to any aqueous medium containing water, buffer solution or nutritional medium suitable for maintaining, transporting, isolating, culturing, propagating, passaging, differentiating or transplanting of cells or tissues.

The aqueous growth medium for cell culture containing one or more salts and optionally one or more sugars may be a liquid or gel that is designed to support the growth of cells, provided it may be mixed with the nanofibrillar cellulose hydrogel so that a homogeneous dispersion is formed. The aqueous growth medium may be suitable for the culture of cells derived from animals, plants, fungi or microorganisms, including bacteria, protists and viruses.

Growth media typically vary e.g. in pH, glucose concentration, growth factors and the present of other nutrients to meet the needs of the cells to be grown in them. Growth media for animal cells typically include essential amino acids, one or more salts, glucose and serum or serum-derived components. The exact composition of the aqueous growth medium is not essential. The aqueous growth medium may comprise various additives such as extra cellular matrix components, serum, growth factors, antibiotics, preservatives and proteins. The aqueous growth medium may be selected depending on the type of cell to be cultured. Examples of suitable aqueous growth media are e.g. Dulbecco's Modified Eagle Medium (DMEM), mTeSR1 (StemCell Technologies), mesenchymal stem cell media (Lonza, Walkersville, Md., #PT-3001), STEMPRO hESC SFM (Invitrogen), Williams' E and differentation media. Further examples of suitable aqueous growth media are e.g. Murashige and Skoog medium and other media suitable for the culture of plant cells and various media suitable for the culture of microbial cells.

The aqueous growth medium may be 1×, i.e. at a concentration that is ready to use for culturing cells. It may also be concentrated, for instance 2×, 4×, 5× or 10×.

Uneven mixing of a nanofibrillar cellulose hydrogel and an aqueous growth medium may cause flocculation. Further, simple mixing e.g. by repeated pipetting or by vortexing the mixture does not result in a sufficiently homogeneous dispersion. Therefore the mixing is performed so that strong shearing forces are imparted on the mixture. The shearing forces should be strong enough in order to disperse the nanofibrillar cellulose homogeneously in the mixture, i.e. to form a homogeneous dispersion. The mixture of the nanofibrillar cellulose hydrogel and the aqueous growth medium thus becomes a homogeneous dispersion. In the homogeneous dispersion, individual rafts of hydrogel may not be observable visually or macroscopically.

A method for reducing the viscosity of a nanofibrillar cellulose hydrogel may thus comprise mixing a nanofibrillar cellulose hydrogel with an aqueous growth medium for cell culture, wherein the aqueous growth medium contains one or more salts and optionally one or more sugars, using shearing forces strong enough in order to disperse the nanofibrillar cellulose homogeneously in the mixture so that a homogeneous dispersion of the nanofibrillar cellulose is formed.

As it may be difficult to ascertain that a hydrogel is completely homogeneous at macroscopic and/or microscopic level, the term "homogeneous" should be understood in this specification as also referring to essentially homogeneous.

The mixing may be carried out until the viscosity of the dispersion is no longer decreasing. In other words, the mixing may be carried out until the viscosity of the dispersion reaches a plateau upon mixing. To this end, it is possible to monitor the viscosity of the dispersion during the mixing.

The Brookfield viscosity of the dispersion may be at least 10% lower, or at least 20% lower, or at least 25% lower, or at least 30% lower, or at least 35% lower, or at least 40% lower, or at least 45% lower, or at least 50% lower than the Brookfield viscosity of the nanofibrillar cellulose hydrogel comprising nanofibrillar cellulose at the same concentration (w/w). In this context, the nanofibrillar cellulose hydrogel comprising nanofibrillar cellulose at the same concentration should be understood as referring to the nanofibrillar cellulose hydrogel that is dispersed in a solution that does not contain one or more salts or sugars instead of the aqueous growth medium but is otherwise comparable to the dispersion, i.e. the nanofibrillar cellulose and its concentration in the hydrogel is the same as in the dispersion. The comparable nanofibrillar cellulose hydrogel may be dispersed or diluted in water. As an example, if the dispersion contains 0.8% (w/w) of nanofibrillar cellulose, the comparable nanofibrillar cellulose hydrogel may contain 0.8% (w/w) nanofibrillar cellulose in water.

The dispersion may have a Brookfield viscosity of up to 15000 mPa·s, or up to 12000 mPa·s, or up to 10000 mPa·s, as measured with a Brookfield viscometer at a temperature of 20° C., with a vane spindle and a measuring speed of 10 rpm.

The method may comprise mixing the nanofibrillar cellulose hydrogel with the aqueous growth medium using an apparatus selected from the group consisting of a blender, a fluidizer, a disperser and a homogenizer. Such apparatuses are capable of creating strong shearing forces, as opposed to e.g. pipetting and vortexing, and thereby dispersing the nanofibrillar cellulose hydrogel homogeneously.

A blender, for instance a Waring blender, may comprise a rotating metal blade for imparting shearing forces. The metal blade may rotate e.g. at a speed of 15-20 m/s, depending on the blender.

A fluidizer may be a high shear fluid processor capable of producing very small particles or droplets for dispersing.

A disperser may be e.g. a single shaft mixer capable of breaking apart or dissolving solid particles in a liquid. Dispersers typically comprise a saw tooth blade rotating at high speed so that the blade imparts high shearing forces to the mixture. The disperser may be, for example, a disperser based on the rotor-stator principle. In such a disperser, the rotor is moved with a high circumferential speed. The rotation produces suction, which pulls the medium into the rotor and then pushes it to the outside with help from the stator's teeth. This process results in the dispersion of the sample.

A homogenizer may apply a pressure difference e.g. by passing the mixture through a small gap in a valve, thereby imparting a pressure difference and high turbulence and shearing forces.

The method may comprise mixing the nanofibrillar cellulose hydrogel with the aqueous growth medium for a time period of at least 5 seconds, or at least 30 seconds, or at least 1 minute, or at least 3 minutes. The time required for the mixing may depend on the apparatus used. For instance, when using a disperser, the time period may be e.g. at least 10 minutes or at least 20 minutes. When using a homogenizer, the mixture may pass through a small gap in a valve very quickly. Several passes in a homogenizer may also be used.

The presence of one or more salts and, to some extent, also other components such as sugars may lower the viscosity of the dispersion, as electrostatic interactions of the salts and other components may affect interactions of nanofibrillar cellulose fibrils with each other and with water.

The term "salt" may be understood in this specification, unless otherwise stated, as referring to any soluble salt, i.e. a salt that readily dissociates into positively and negatively charged ions in an aqueous medium. It may, in principle, be an inorganic salt or an organic salt. Examples of such salts are e.g. chlorides such as NaCl, KCl, $MgCl_2$ and $CaCl_2$, sulfates such as $MgSO_4.7H_2O$, $CuSO_4.5H_2O$, $ZnSO_4.7H_2O$ and $FeSO_4.7H_2O$, $NaH_2PO_4$, $KH_2PO_4$ and other soluble phosphate, hydrogen phosphate and dihydrogen phosphate salts, bicarbonates such as $NaHCO_3$, nitrates such as $Ca(NO_3)_2$ and $Fe(NO_3)_3.9H_2O$, ammonium salts such as $NH_4Cl$, citrates such as sodium citrate, acetates, pyruvates such as sodium pyruvate, and choline salts such as choline chloride. Zwitterions such as amino acids, peptides and proteins may not be considered to be salts in the context of this specification. The term "salt" or "a salt" may also refer to any mixture of two or more salts. The salt may also have any valency, i.e. it may be e.g. monovalent, divalent, trivalent or tetravalent.

The salt may be selected from the group consisting of NaCl, KCl, $MgCl_2$, $CaCl_2$, $MgSO_4.7H_2O$, $CuSO_4.5H_2O$, $ZnSO_4.7H_2O$, $FeSO_4.7H_2O$, $NaH_2PO_4$, $KH_2PO_4$, $NaHCO_3$, $Ca(NO_3)_2$, $Fe(NO_3)_3.9H_2O$, $NH_4Cl$, sodium citrate, sodium pyruvate and choline chloride.

The aqueous growth medium may comprise at least about 20 meq/l, or at least about 250 meq/l, or about 20-400 meq/l, or about 250-350 meq/l, or about 280-320 meq/l of ions of one or more salts. Even relatively low concentrations of one or more salts present in the aqueous growth medium may be capable of reducing the viscosity of the nanofibrillar cellulose hydrogel. However, the salt concentration of many aqueous growth media is determined by the need to maintain a suitable osmotic pressure and the physiological and structural integrity of cells. A suitable concentration of ions of one or more salts may be e.g. that providing an osmotic pressure equivalent of a physiological salt solution. A decrease in the viscosity of the nanofibrillar cellulose hydrogel may be observed already at relatively low concentrations of salt ions. The salt may also be selected so that it is suitable for cell culture (e.g. non-toxic).

In an embodiment, the salt is NaCl. The aqueous growth medium may comprise at least about 20 meq/l, or at least about 250 meq/l, or about 20-400 meq/l, or about 250-350 meq/l, or about 280-320 meq/l of $Na^+$ and $Cl^-$ ions.

The term "eq" or "equivalent" may be understood in this specification, unless otherwise stated, as referring to an amount of a salt (one or more salts) multiplied by its valence. The unit of eq may be mole (mol). For instance, 0.9% saline (aqueous solution of NaCl) contains 154 meq/l or 154 mmol/l of $Na^+$ and 154 meq/l of $Cl^-$, thus amounting to 308 meq/l of ions in total. 154 mmol/l of $Ca^{2+}$ equals 308 meq/l.

Thus, the aqueous growth medium may comprise at least about 10 mmol/l, or at least about 125 mmol/l, or about 0.5-200 mmol/l, or about 125-175 mmol/l, or about 140-160 mmol/l of NaCl.

The dispersion of the nanofibrillar cellulose hydrogel and the aqueous growth medium may comprise at least about 10 meq/l, or at least about 20 meq/l, or at least about 50 meq/l, or at least about 70 meq/l, or at least about 90 meq/l, or at least about 100 meq/l, or at least about 250 meq/l, or about 10-400 meq/l, or about 10-300 meq/l, or about 20-200 meq/l, or about 50-150 meq/l, or about 70-400 meq/l, or about 250-350 meq/l, or about 280-320 meq/l of ions of one or more salts.

The dispersion may comprise at least about 10 meq/l, or at least about 20 meq/l, or at least about 50 meq/l, or at least about 70 meq/l, or at least about 90 meq/l, or at least about 100 meq/l, or at least about 250 meq/l, or about 10-400 meq/l, or about 10-300 meq/l, or about 20-200 meq/l, or about 50-150 meq/l, or about 70-400 meq/l, or about 250-350 meq/l, or about 280-320 meq/l of $Na^+$ and $Cl^-$ ions.

The dispersion may comprise at least about 5 mmol/l, or at least about 50 mmol/l, or at least about 125 mmol/l, or about 5-200 mmol/l, or about 125-175 mmol/l, or about 140-160 mmol/l of NaCl.

Aqueous growth media typically contain one or more sugars as a source of carbon and energy. However, the sugar contained by aqueous growth media may also be able to decrease the viscosity of nanofibrillar cellulose hydrogel. The effect of the one or more sugars may be synergistic with the effect of the one or more salts.

The aqueous growth medium may comprise at least about 0.1 mmol/l, or at least about 1 mmol/l, or at least about 5 mmol/l, or about 0.1-500 mmol/l, or about 1-200 mmol/l, or about 5-55 mmol/l of one or more sugars. The sugar may be e.g. glucose, galactose, fructose, sucrose or any mixture thereof. These sugars are typically D-sugars. For instance, growth media for animal cells typically comprise about 5-55 mmol/l of D-glucose.

The dispersion of the nanofibrillar cellulose hydrogel and the aqueous growth medium may comprise at least about 0.1 mmol/l, or at least about 1 mmol/l, or at least about 1.3 mmol/l, or at least about 5 mmol/l, or about 0.1-500 mmol/l, or about 1-200 mmol/l, or about 1.3-55 mmol/l, or about 5-55 mmol/l of one or more sugars.

The nanofibrillar cellulose may be native nanofibrillar cellulose. It may also be anionic nanofibrillar cellulose. Native and anionic nanofibrillar cellulose hydrogels may behave slightly differently upon mixing with the aqueous growth medium.

The nanofibrillar cellulose hydrogel may comprise about 0.05%-4% (w/w) of nanofibrillar cellulose.

The method may comprise mixing the nanofibrillar cellulose hydrogel and the aqueous growth medium at a volume ratio in the range of about 9:1-1:9, or about 3:1-1:1. The volume ratio should be understood throughout this specification so that at a volume ratio of 9:1, 9 parts (volumes) of the nanofibrillar cellulose hydrogel are mixed with 1 part (volume) of the aqueous growth medium. The volume ratio may depend e.g. on the concentration of the aqueous growth medium. For instance, if the aqueous growth medium is concentrated, e.g. 10×, the volume ratio of 9:1 gives a dispersion containing 1× aqueous growth medium. The volume ratio may also be selected such that it allows the growth of cells in the dispersion. The dispersion may contain 1× aqueous growth medium, but it may also contain less, e.g. 0.5× or 0.3× aqueous growth medium. Fresh growth medium may be brought into contact with the dispersion during cell culture to increase the concentration of the growth medium.

The dispersion may comprise about 0.05%-2.5% (w/w), or about 0.5-1.7% (w/w), or about 1.0-1.7% (w/w), about 1.0-1.5% (w/w) of nanofibrillar cellulose.

The method may comprise mixing the nanofibrillar cellulose hydrogel and the aqueous growth medium to form a dispersion giving a pipetting error of less than 5% (v/v) upon pipetting. The pipetting error may be measured using a pipette, such as a piston pipette, and a pipetting volume of 500 μl. A graduated 1250 μl pipette tip may be used with the pipette. The pipette tip may be non-adhesive material, such as plastic, e.g. polypropylene. An example of a suitable tip is StarLab TipOne RPT. The pipette should be calibrated. The pipetting error may be estimated by pipetting 500 μl of the dispersion to a balance and recording the weight of the dispersion obtained at least four times to calculate the actual volume pipetted. The difference between 500 μl and the average of the actual volumes pipetted is calculated; this difference is the pipetting error. The pipetting error may also be determined in a similar manner using a pipetting robot.

The method may also comprise mixing the nanofibrillar cellulose hydrogel and the aqueous growth medium at a volume ratio at which the dispersion gives a pipetting error of less than 5% (v/v) upon pipetting.

The storage modulus of the dispersion may be e.g. less or equal to about 200 Pa, or about 50-0.3 Pa.

A dispersion comprising a nanofibrillar cellulose hydrogel and an aqueous growth medium for cell culture is also disclosed, wherein the aqueous growth medium contains one or more salts and optionally one or more sugars, and wherein the nanofibrillar cellulose hydrogel is homogeneously dispersed in the dispersion.

Further, a dispersion obtainable by one or more embodiments of the method is disclosed.

The dispersion may also be considered to meet the definition of a nanofibrillar cellulose hydrogel.

The dispersion may contain at least about 10 meq/l, or at least about 20 meq/l, or at least about 50 meq/l, or at least about 70 meq/l, or at least about 90 meq/l, or at least about 100 meq/l, or at least about 280 meq/l, or about 10-400 meq/l, or about 10-300 meq/l, or about 20-200 meq/l, or about 50-150 meq/l, or about 70-400 meq/l, or about 250-350 meq/l, or about 280-320 meq/l of ions of one or more salts.

The dispersion may comprise at least about 5 mmol/l, or at least about 10 mmol/l, or at least about 25 mmol/l, or at least about 35 mmol/l, or at least about 45 mmol/l, or at least about 50 mmol/l, or at least about 125 mmol/l, or about 5-200 mmol/l, or about 10-200 mmol/l, or about 25-200 mmol/l, or about 35-200 mmol/l, or about 45-200 mmol/l, or about 50-200 mmol/l, or about 125-175 mmol/l, or about 140-160 mmol/l of NaCl.

The dispersion may comprise at least about 0.1 mmol/l, or at least about 1 mmol/l, or at least 1.3 mmol/l, or at least about 5 mmol/l, or about 0.1-500 mmol/l, or about 1-200 mmol/l, or about 1.3-55 mmol/l, or about 5-55 mmol/l of one or more sugars.

The dispersion may comprise the nanofibrillar cellulose hydrogel and the aqueous growth medium at a volume ratio in the range of about 9:1-1:9, or 3:1-1:1.

The Brookfield viscosity of the dispersion may be at least 10% lower, or at least 20% lower, or at least 25% lower, or at least 30% lower, or at least 35% lower, or at least 40% lower, or at least 45% lower, or at least 50% lower than the Brookfield viscosity of the nanofibrillar cellulose hydrogel comprising nanofibrillar cellulose at the same concentration (w/w).

The dispersion may have a Brookfield viscosity of up to about 15000 mPa·s, or up to about 12000 mPa·s, or up to about 10000 mPa·s, as measured with a Brookfield viscometer at a temperature of 20° C., with a vane spindle and a measuring speed of 10 rpm.

The storage modulus of the dispersion may be e.g. less or equal to about 200 Pa, or about 50-0.3 Pa.

The dispersion may give a pipetting error of less than 5% (v/v) upon pipetting. The pipetting error may be measured as described above.

The nanofibrillar cellulose may be native nanofibrillar cellulose. It may also be anionic nanofibrillar cellulose.

The dispersion may comprise about 0.05%-2.5% (w/w), or about 0.5-1.7% (w/w), or about 1.0-1.7% (w/w), or about 1.0-1.5% (w/w) of nanofibrillar cellulose.

The dispersion may be a ready-to-use mixture or a stock mixture to be diluted with a further amount of aqueous growth medium before use.

When the dispersion is used for maintaining or culturing cells, the cellulose nanofibers can be degraded enzymatically by adding enzymes mixtures comprising all necessary enzymes for the total degradation of cellulose molecules as well as other wood derived components in it, such as hemicelluloses. Suitable enzymes are, for example, designed enzyme mixtures for the NFC in question and commercially available cellulase-hemicellulase preparations. Degrading of the NFC hydrogel may be conducted as disclosed e.g. in WO2014/049204, including page 16 line 14-page 28, line 19.

The dispersion according to one or more embodiments for use in therapy is disclosed.

The dispersion according to one or more embodiments for use in transplanting of cells or tissues is disclosed.

A multiwell plate comprising one or more embodiments of the dispersion is also disclosed. One or more wells of the multiwell plate may be pre-filled with the dispersion.

A kit comprising one or more embodiments of the dispersion is disclosed. The kit may further comprise instructions for use and optionally other components, such as an aqueous growth medium.

A kit comprising a nanofibrillar cellulose hydrogel; an aqueous growth medium for cell culture containing one or more salts and optionally one or more sugars; and instructions for reducing the viscosity of the nanofibrillar cellulose hydrogel is disclosed.

The instructions may include instructions for reducing the viscosity of the nanofibrillar cellulose hydrogel according to one or more embodiments of the method described in this specification. In this context, the nanofibrillar cellulose hydrogel and the aqueous growth medium may be any nanofibrillar cellulose hydrogel and any aqueous growth medium described in this specification.

The use of an aqueous growth medium for cell culture containing one or more salts and optionally one or more sugars for reducing the viscosity of a nanofibrillar cellulose hydrogel is disclosed.

The use of the dispersion according to one or more embodiments in a dispenser, such as a pipet, an automatic dispenser or a pipetting robot, is disclosed.

The aqueous growth medium for cell culture containing one or more salts and optionally one or more sugars may be a liquid or gel that is designed to support the growth of cells, provided it may be mixed with the nanofibrillar cellulose hydrogel so that a homogeneous dispersion is formed. The aqueous growth medium may be suitable for the culture of cells derived from animals, plants, fungi or microorganisms, including bacteria, protists and viruses.

Growth media typically vary e.g. in pH, glucose concentration, growth factors and the present of other nutrients to meet the needs of the cells to be grown in them. Growth media for animal cells typically include essential amino acids, one or more salts, glucose and serum or serum-derived components. The exact composition of the aqueous growth medium is not essential. The aqueous growth medium may comprise various additives such as extra cellular matrix components, serum, growth factors, antibiotics, preservatives and proteins. Some of the additives included for the end use may be added to the obtained dispersion of nanofibrillar cellulose hydrogel and the growth medium, for example directly before use. The aqueous growth medium may be selected depending on the type of cell to be cultured. Examples of suitable aqueous growth media are e.g. Dulbecco's Modified Eagle Medium (DMEM), mTeSR1 (StemCell Technologies), mesenchymal stem cell media (Lonza, Walkersville, Md., #PT-3001), STEMPRO hESC SFM (Invitrogen), Williams' E and differentation media. Further examples of suitable aqueous growth media are e.g. Murashige and Skoog medium and other media suitable for the culture of plant cells and various media suitable for the culture of microbial cells.

The aqueous growth medium may be 1×, i.e. at a concentration that is ready to use for culturing cells. It may also be concentrated, for instance 2×, 4×, 5× or 10×.

The aqueous growth medium for cell culture may contain at least about 20 meq/l, or at least about 250 meq/l, or about 20-400 meq/l, or about 250-350 meq/l, or about 280-320 meq/l of ions of one or more salts.

In an embodiment, the salt is NaCl. The aqueous growth medium may comprise at least about 20 meq/l, or at least about 250 meq/l, or about 20-400 meq/l, or about 250-350 meq/l, or about 280-320 meq/l of $Na^+$ and $Cl^-$ ions. Thus, the aqueous growth medium may comprise at least about 10 mmol/l, or at least about 125 mmol/l, or about 10-200 mmol/l, or about 125-175 mmol/l, or about 140-160 mmol/l of NaCl.

The aqueous growth medium may comprise at least about 0.1 mmol/l, or at least about 1 mmol/l, or at least about 5 mmol/l, or about 0.1-500 mmol/l, or about 1-200 mmol/l, or about 5-55 mmol/l of one or more sugars. The sugar may be e.g. glucose, galactose, fructose, sucrose or any mixture thereof. These sugars are typically D-sugars. For instance, growth media for animal cells typically comprise about 5-55 mmol/l of D-glucose.

The nanofibrillar cellulose hydrogel and the aqueous growth medium may be mixed at a volume ratio in the range of about 9:1-1:9, or 3:1-1:1.

The nanofibrillar cellulose may be native nanofibrillar cellulose. It may also be anionic nanofibrillar cellulose.

The nanofibrillar cellulose hydrogel may comprise about 0.05%-4% (w/w) of nanofibrillar cellulose.

The dispersion may be a ready-to-use mixture or a stock mixture to be diluted with a further amount of growth medium before use.

When the dispersion is used for maintaining or culturing cells, the cellulose nanofibers can be degraded enzymatically by adding enzymes mixtures comprising all necessary enzymes for the total degradation of cellulose molecules as well as other wood derived components in it, such as hemicelluloses. Suitable enzymes are, for example, designed enzyme mixtures for the NFC in question and commercially available cellulase-hemicellulase preparations. Degrading of the NFC hydrogel may be conducted as disclosed e.g. in WO2014/049204, including page 16 line 14-page 28, line 19.

The embodiments of the invention described hereinbefore may be used in any combination with each other. Several of the embodiments may be combined together to form a further embodiment of the invention. A method, a composition or a use, to which the invention is related, may comprise at least one of the embodiments of the invention described hereinbefore.

A technical effect of one or more embodiments is that when an aqueous growth medium is mixed with nanofibrillar cellulose hydrogel prior to use, its viscosity decreases and may subsequently improve the accuracy of dosing, for instance when using an automatic dispenser or a pipetting robot, due to enhanced handling. Further, other growth factors may be easier to add in situ. The efficiency of well plate filling may also improve.

A technical effect of one or more embodiments is that the viscosity can be reduced without significant adverse effects on other properties of the hydrogel.

A technical effect of one or more embodiments is that the viscosity of the nanofibrillar cellulose hydrogel may be reduced without substantially reducing the consistency.

A technical effect of one or more embodiments is that in the dispersion of the NFC hydrogel and the aqueous growth medium the nanocellulose fibrils may be more accessible to enzymatic degradation. The improved accessibility may allow more efficient liberation of cultured cells from the dispersion.

A technical effect of one or more embodiments is that compared to continuous hydrogel structure, the dispersion of the NFC hydrogel and the aqueous growth medium may be less prone to breaking into clumps and channel formation e.g. upon further addition of growth medium. Channel formation may result in undesired settling of the cells via channels to the bottom of the culture.

EXAMPLES

Reference will now be made in detail to the embodiments, an example of which is illustrated in the accompanying drawing.

The description below discloses some embodiments in such a detail that a person skilled in the art is able to utilize the invention based on the disclosure. Not all steps of the embodiments are discussed in detail, as many of the steps will be obvious for the person skilled in the art based on this specification.

Example 1—Preparing a Dispersion of a Native Nanofibrillar Cellulose Hydrogel and DMEM Growth Medium 2000 g of wet native cellulose pulp obtained from bleached birch pulp was filtered and the solid mass was diluted with 0.01M aqueous HCl and to obtain a suspension having a dry matter content of approx. 1% by weight. The suspension was allowed to stand for approx. 15 min with occasional agitation. The suspension was then filtered, washed twice with deionized water and filtered. Then the solid mass was suspended in a 0.005 M aqueous $NaHCO_3$ solution to obtain a suspension having a dry matter content of approx. 1% by weight, the pH of the obtained suspension was adjusted between 8 and 9 with 1 M aqueous NaOH solution and the obtained suspension was allowed to stand for 15 min with occasional agitation. The suspension was filtered and the solid mass was washed with deionized water until the conductivity of the filtrate was less than 20 μS/cm. The final conductivity was 8 μS/cm and pH 8.4.

Washed pulp was pre-grinded with PFI grinder. Standard refining was done until target SR value>75 was reached. The SR value after the pre-refining was 80.2.

The pre-refined sample was diluted to 1.7 w % consistency and followed by fibrillation in Microfluidics Fluidizer (M-7115-30), once trough APM+200 μm chambers and through APM+100 μm chambers until the turbidity was below the target level<200 NTU. The final turbidity for the product, Sample 1, was 136 NTU.

To verify the preferred gel properties, rheological measurements of the samples in the form of nanofibrillar cellulose hydrogels were carried out with a stress controlled rotational rheometer. The Frequency sweep measurement of Sample 1 was performed in 0.5 wt % to verify that the gel strength is sufficient, which is, a loss tangent (tan δ) is less than 1. The loss tangent (tan δ) was 0.20 and the storage modulus (G') was 2 Pa at a frequency of 1 rad/s, 1% strain.

1.69% native nanofibrillar cellulose hydrogel in water was diluted by adding 1× Dulbecco's Modified Eagle Medium (DMEM, Gibco) containing 110 mM NaCl and 1 g/l of glucose and by mixing with a Bamix® mixer for 30 s. The dispersion obtained contained 1.2%, 0.9%, or 0.5% (w/w) of nanofibrillar cellulose based on the total weight of the dispersion. For comparison, the same hydrogel was diluted with water so that the concentration of the dispersion was 1.2% (w/w) of nanofibrillar cellulose based on the total weight of the dispersion.

Pipetting errors for these dispersions were measured using graduated 1250 μl polypropylene pipette tips (StarLab TipOne RPT) with a piston pipette and a pipetting volume of 500 μl. The pipetting error was estimated by pipetting 500 μl of the dispersion to a balance and recording the weight of the dispersion obtained at least four times to calculate the actual volume pipetted. The difference between 500 μl and the average of the actual volumes pipetted was calculated as the pipetting error.

Brookfield viscosities of the dispersions were measured as follows. A vane spindle (number 73) was selected and the Brookfield viscosity measuring apparatus (Brookfield RVDV-III) was started. The diluted sample mass was added to a 250 ml beaker and the temperature was adjusted to 20° C.±1° C., heated if necessary and mixed. The spindle was inserted in the beaker and measuring was started. The program registered 300 points starting with 0.5 rpm speed, then 300 points with 5 rpm and 10 rpm, and 100 points with rpm and 100 rpm speeds. Relative viscosity was measured from each sample mass twice. Mean value and standard deviation were calculated for each sample, from results obtained from parallel measurements during last 5 seconds.

The pipetting errors and viscosities measured are shown in Table 1 and as a graph in FIG. 1. The error bars denote coefficient of variation.

TABLE 1

Pipetting errors and viscosities measured for different dispersions of nanofibrillar cellulose hydrogel and DMEM/water

| Sample | 1.2% NFC in DMEM | 0.9% NFC in DMEM | 0.5% NFC in DMEM | 1.2% NFC in water |
|---|---|---|---|---|
| Average volume pipetted, μl | 478.1 | 486.3 | 494.3 | 457.7 |
| Difference from 500 μl | −4.38% | −2.75% | −1.15% | −8.47% |
| Brookfield viscosity, 10 rpm, mPa · s | 10615 | 7350 | 1985 | 23515 |

It is obvious to a person skilled in the art that with the advancement of technology, the basic idea of the invention may be implemented in various ways. The invention and its embodiments are thus not limited to the examples described above; instead they may vary within the scope of the claims.

The invention claimed is:

1. A method for reducing the viscosity of a nanofibrillar cellulose hydrogel, wherein the method comprises mixing a nanofibrillar cellulose hydrogel with an aqueous growth medium for cell culture, wherein the aqueous growth medium includes one or more salts and optionally one or more sugars, using shearing forces strong enough in order to disperse the nanofibrillar cellulose homogeneously in the mixture so that a homogeneous dispersion of the nanofibrillar cellulose is formed, wherein individual rafts of hydrogel are not observable visually or macroscopically in the homogeneous dispersion, the nanofibrillar cellulose hydrogel comprising about 0.05%-4% (w/w) of nanofibrillar cellulose.

2. The method according to claim 1, wherein the method comprises mixing the nanofibrillar cellulose hydrogel with the aqueous growth medium using an apparatus selected from the group consisting of a blender, a fluidizer, a disperser and a homogenizer.

3. The method according to claim 1, wherein the aqueous growth medium comprises at least about 1-400 meq/l of ions of one or more salts.

4. The method according to claim 1, wherein the dispersion of the nanofibrillar cellulose hydrogel and the aqueous growth medium comprises about 10-400 meq/l of ions of one or more salts.

5. The method according to claim 1, wherein the aqueous growth medium comprises about 0.1-500 mmol/l of one or more sugars.

6. The method according to claim 1, wherein the dispersion of the nanofibrillar cellulose hydrogel and the aqueous growth medium comprises 0.1-500 mmol/l of one or more sugars.

7. The method according to claim 1, wherein the nanofibrillar cellulose is native or anionic nanofibrillar cellulose.

8. The method according to claim 1, further comprising mixing the nanofibrillar cellulose hydrogel and the aqueous growth medium at a volume ratio in the range of about 9:1-1:9.

9. The method according to claim 1, further comprising mixing the nanofibrillar cellulose hydrogel and the aqueous growth medium to form a dispersion giving a pipetting error of less than 5% (v/v) upon pipetting.

10. The method according to claim 1, further comprising mixing the nanofibrillar cellulose hydrogel and the aqueous growth medium until the viscosity of the dispersion no longer decreases.

11. A dispersion comprising a nanofibrillar cellulose hydrogel and an aqueous growth medium for cell culture, wherein the aqueous growth medium includes one or more salts and optionally one or more sugars, and wherein the nanofibrillar cellulose hydrogel is homogeneously dispersed in the aqueous growth medium and wherein individual rafts of hydrogel are not observable visually or macroscopically, wherein the dispersion comprises about 0.05%-2.5% (w/w) of nanofibrillar cellulose.

12. The dispersion according to claim 11, wherein the dispersion comprises about 10-400 meq/l of ions of one or more salts.

13. The dispersion according to claim 11, wherein the dispersion comprises about 0.1-500 mmol/l of one or more sugars.

14. The dispersion according to claim 11, wherein the dispersion comprises the nanofibrillar cellulose hydrogel and the aqueous growth medium at a volume ratio in the range of about 9:1-1:9.

15. The dispersion according to claim 11, wherein the dispersion has a Brookfield viscosity of up to 15000 mPa·s, as measured with a Brookfield viscometer at a temperature of 20° C., with a vane spindle and a measuring speed of 10 rpm.

16. The dispersion according to claim 11, wherein the Brookfield viscosity of the dispersion may be at least 10% lower than the Brookfield viscosity of the nanofibrillar cellulose hydrogel comprising nanofibrillar cellulose at the same concentration (w/w).

17. The dispersion according to claim 11, wherein the storage modulus of the dispersion is less or equal to about 200 Pa.

18. The dispersion according to claim 11, wherein the dispersion gives a pipetting error of less than 5% (v/v) upon pipetting.

19. The dispersion according to claim 11, wherein the nanofibrillar cellulose is native or anionic nanofibrillar cellulose.

20. A multiwell plate or a kit comprising the dispersion according to claim 11.

* * * * *